(12) United States Patent
Dedick et al.

(10) Patent No.: US 11,963,529 B1
(45) Date of Patent: *Apr. 23, 2024

(54) APPLICATION OF STRUCTURALLY ALTERED GAS MOLECULES TO ENHANCE PRODUCTION OF ADENOSINE TRIPHOSPHATE IN LIVING ORGANISMS WITH NO INCREASE IN REACTIVE OXYGEN SPECIES

(71) Applicants: H2Plus LLC, San Diego, CA (US); H2Plus Operations, LLC, San Diego, CA (US)

(72) Inventors: Gene Dedick, Grand Junction, CO (US); Jared Roberts, Grand Junction, CO (US)

(73) Assignees: H2Plus LLC, San Diego, CA (US); H2Plus Operations, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/376,765

(22) Filed: Oct. 4, 2023

Related U.S. Application Data

(63) Continuation-in-part of application No. PCT/US2022/044167, filed on Sep. 21, 2022, which is a continuation of application No. 17/487,613, filed on Sep. 28, 2021, now Pat. No. 11,384,440, application No. 18/376,765 is a continuation-in-part of application No. PCT/US2022/044168, filed on Sep. 21, 2022, which is a continuation of application No. 17/743,632, filed on May 13, 2022, now Pat. No. 11,634,823, which is a continuation of application No. 17/487,613, filed on Sep. 28, 2021, now Pat. No. 11,384,440, said application No. PCT/US2022/044168 is a continuation of application No. 17/487,613, filed on Sep. 28, 2021, now Pat. No. 11,384,440.

(51) Int. Cl.
| | |
|---|---|
| *A01N 59/00* | (2006.01) |
| *A01P 21/00* | (2006.01) |
| *A61K 33/00* | (2006.01) |
| *A61P 3/00* | (2006.01) |
| *C25B 1/044* | (2021.01) |

(52) U.S. Cl.
CPC .............. *A01N 59/00* (2013.01); *A01P 21/00* (2021.08); *A61K 33/00* (2013.01); *A61P 3/00* (2018.01); *C25B 1/044* (2021.01)

(58) Field of Classification Search
CPC ......... A01N 59/00; A01P 21/00; A61K 33/00; A61P 3/00; C25B 1/044
See application file for complete search history.

(56) References Cited

U.S. PATENT DOCUMENTS

| | | | |
|---|---|---|---|
| 6,974,561 B1* | 12/2005 | Thomason | A23K 30/10 204/554 |
| 11,384,440 B1 | 7/2022 | Roberts et al. | |
| 11,634,823 B2 | 4/2023 | Roberts et al. | |

OTHER PUBLICATIONS

Johnson TA, Jinnah HA and Kamatani N, "Shortage of Cellular ATP as a Cause of Diseases and Strategies to Enhance ATP", Frontiers in Pharmacology, 2019, 10:98, 1-19. (Year: 2019).*

* cited by examiner

*Primary Examiner* — Mina Haghighatian
*Assistant Examiner* — Nathan W Schlientz
(74) *Attorney, Agent, or Firm* — Georgiy L. Khayet

(57) ABSTRACT

Methods and systems for enhancing production of adenosine triphosphate (ATP) in living organisms are provided. An example method includes generating structurally altered gas molecules from water. The structurally altered gas molecules have a higher probability of attraction of electrons into areas adjunct to the structurally altered gas molecules than molecules of the water. The method further includes infusing the structurally altered gas molecules into a living organism. Upon being infused, the structurally altered gas molecules cause an increase of production of the ATP in the living organism.

2 Claims, 13 Drawing Sheets

| Variable | Horse 1 | | | Horse 2 | | | Normal Range |
|---|---|---|---|---|---|---|---|
| | day 0 | day 10 | day 21 | day 0 | day 10 | day 21 | |
| White blood cells | 11,800 | 8,400 | 8,500 | 8,200 | 8,000 | 6,400 | $5.5$–$10.5 \times 10^3$ |
| PCV | 50 | 46 | 44 | 42 | 48 | 37 | 30-45 |
| Hemoglobin | 18.7 | 17.1 | 16.4 | 15.2 | 17.3 | 13.7 | 11-16 |
| Total Protein | 6.4 | 6.7 | 6.2 | 6.5 | 6.4 | 6.0 | 5.6-7.5 |
| SDH | 4 | 2 | 2 | 1 | 1 | 1 | 4-14 |
| GGT | 25 | 26 | 22 | 35 | 27 | 20 | 14-40 |
| AST | 270 | 308 | 315 | 242 | 272 | 225 | 170-435 |
| CK | 394 | 282 | 257 | 223 | 585 | 215 | 30-357 |
| BUN | 18 | 18 | 16 | 19 | 18 | 17 | 10-27 |
| Creatinine | 1.1 | 0.8 | 0.8 | 1.1 | 1.0 | 0.9 | 0.8-1.9 |
| Glucose | 100 | 78 | 91 | 59 | 91 | 90 | 47-110 |
| Albumin | 4.2 | 4.2 | 3.9 | 4.2 | 4.2 | 3.7 | 2.8-4.1 |
| Globulin | 2.2 | 2.5 | 2.3 | 2.3 | 2.2 | 2.3 | 1.8-4.1 |
| Calcium | 12.3 | 12.9 | 12.0 | 12.0 | 12.9 | 11.8 | 10.7-14.1 |
| Phosphate | 3.0 | 3.5 | 3.3 | 3.0 | 2.8 | 2.8 | 2.2-4.7 |
| Bilirubin | 1.4 | 1.2 | 1.3 | 2.0 | 1.4 | 1.3 | 0.6-2.9 |
| Sodium | 146 | 143 | 141 | 140.0 | 140 | 143 | 132-141 |
| Potassium | 2.3 | 4.1 | 3.7 | 4.0 | 4.3 | 3.1 | 2.4-5.6 |
| Chloride | 105 | 104 | 102 | 100.0 | 104 | 104 | 96-106 |

FIG. 4

| Average grams per plant | Seed Day | Grams per Plant per Total Days of Growth |
|---|---|---|
| 21.7 | Day 1 | 0.314493 |
| 30.8 | Day 8 | 0.446377 |
| 36 | Day 16 | 0.537313 |
| 44.3 | Day 22 | 0.651471 |
| 38.5 | Day 23 | 0.542254 |
| 29.6 | Day 29 | 0.422857 |
| 43.6 | Day 36 | 0.631884 |
| 62 | Day 42 | 0.873239 |
| 57.5 | Day 43 | 0.809859 |
| 65.1 | Day 49 | 0.943478 |
| 72 | Day 50 | 1.028571 |
| 61.5 | Day 51 | 0.82 |
| 52.9 | Day 72 | 0.867213 |
| 53.9 | Day 76 | 0.842188 |
| 49.3 | Day 77 | 0.758462 |
| 36.2 | Day 106 | 0.84186 |
| 44 | Day 107 | 0.93617 |
| 51.9 | Day 112 | 1.059184 |
| 48.9 | Day 119 | 1.164286 |
| 39.8 | Day 119 | 0.829167 |
| 36.6 | Day 127 | 0.665455 |
| 42.3 | Day 127 | 0.742105 |
| 50.7 | Day 142 | 1.078723 |
| 50.7 | Day 146 | 1.013333 |
| 41.2 | Day 150 | 0.749091 |

APPLICATION OF STRUCTURALLY ALTERED GAS MOLECULES TO ENHANCE PRODUCTION OF ADENOSINE TRIPHOSPHATE IN LIVING ORGANISMS WITH NO INCREASE IN REACTIVE OXYGEN SPECIES

TECHNICAL FIELD

This disclosure relates to methods for application of a structurally altered gas molecule to enhance production of adenosine triphosphate (ATP) in living organisms with no increase in reactive oxygen species.

BACKGROUND

All living things require energy to function. While different organisms acquire this energy in different ways, they store (and use it) in the same way. ATP is how cells store and use energy. These storage molecules are produced in the mitochondria, tiny organelles found in eukaryotic cells sometimes called the "powerhouse" of the cell.

A living cell cannot store significant amounts of free energy. Excess free energy would result in an increase of heat in the cell, which would result in excessive thermal motion that could damage or even destroy the cell. Rather, a cell must be able to handle that energy in a way that enables the cell to store energy safely and release it for use only as needed. Living cells accomplish this by using the compound ATP. ATP is often called the "energy currency" of the cell, and, like other fungible examples of currency, this versatile compound can be used to fill any energy need of the cell. It functions similarly to a rechargeable battery. When ATP is broken down, usually by the removal of its terminal phosphate group, energy is released. The energy is used to do work by the cell, usually by the released phosphate binding to another molecule, thereby activating that molecule's ability to do the intended work.

For example, in the mechanical work of muscle contraction, ATP supplies the energy to move the contractile muscle proteins. Recall the active transport work of the sodium-potassium pump in cell membranes. ATP alters the structure of the integral protein that functions as the pump, changing its affinity for sodium and potassium. In this way, the cell performs work, pumping ions against their electrochemical gradients.

SUMMARY

This summary is provided to introduce a selection of concepts in a simplified form that are further described in the Detailed Description below. This summary is not intended to identify key features or essential features of the claimed subject matter, nor is it intended to be used as an aid in determining the scope of the claimed subject matter.

According to one example embodiment of the present disclosure, a method for enhancing production of ATP in living organisms is provided. The method may include generating structurally altered gas molecules from water. The structurally altered gas molecules have a higher probability of attraction of electrons into areas adjunct to the structurally altered gas molecules than molecules of the water. The method may further include infusing the structurally altered gas molecules into a living organism. Upon being infused, the structurally altered gas molecules cause an increase of production of the ATP in the living organism.

According to another embodiment of the present disclosure, a system for enhancing production of ATP in living organisms is provided. The system may include a magnetic field generator and an electric field generator configured to apply the magnetic field and the electric field to water to cause generation of structurally altered gas molecules from the water. The structurally altered gas molecules have a higher probability of attraction of electrons into areas adjunct to the structurally altered gas molecules than molecules of the water. The system may further include a diffuser for infusing the structurally altered gas molecules into a living organism. Upon being infused, the structurally altered gas molecules cause an increase of production of the ATP in the living organism.

Other example embodiments of the disclosure and aspects will become apparent from the following description taken in conjunction with the following drawings.

BRIEF DESCRIPTION OF DRAWINGS

Exemplary embodiments are illustrated by way of example and not limitation in the figures of the accompanying drawings, in which like references indicate similar elements.

FIG. 4 shows a table of blood test results of horses, according to an example embodiment.

FIG. 11 shows a table illustrating average grams per plant, a seed date, and grams per plant per total days of growth, according to an example embodiment.

DETAILED DESCRIPTION

Figure 1:
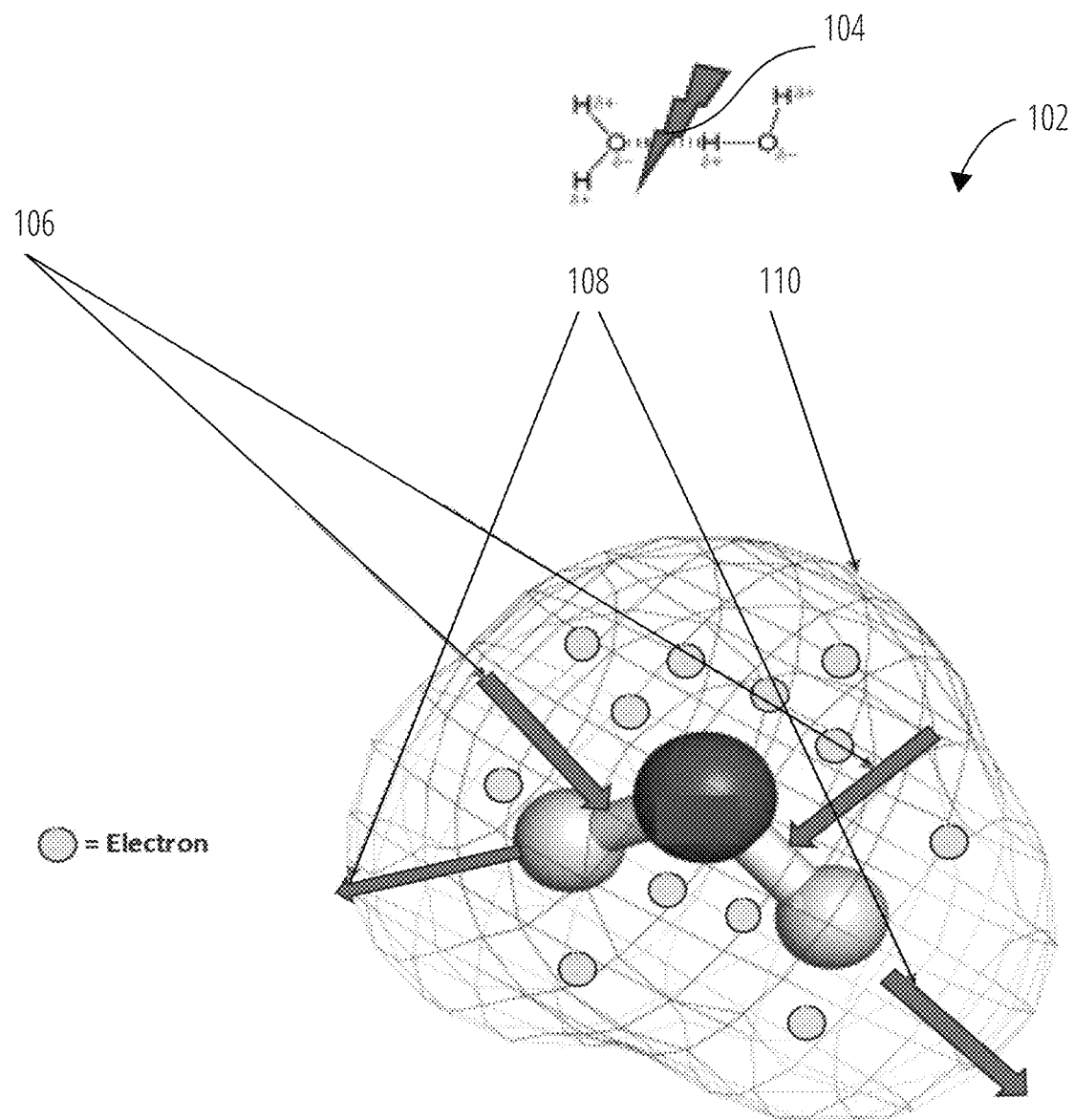
FIG. 1 shows a structurally altered gas molecule according to the method of the present disclosure.
Figure 2:
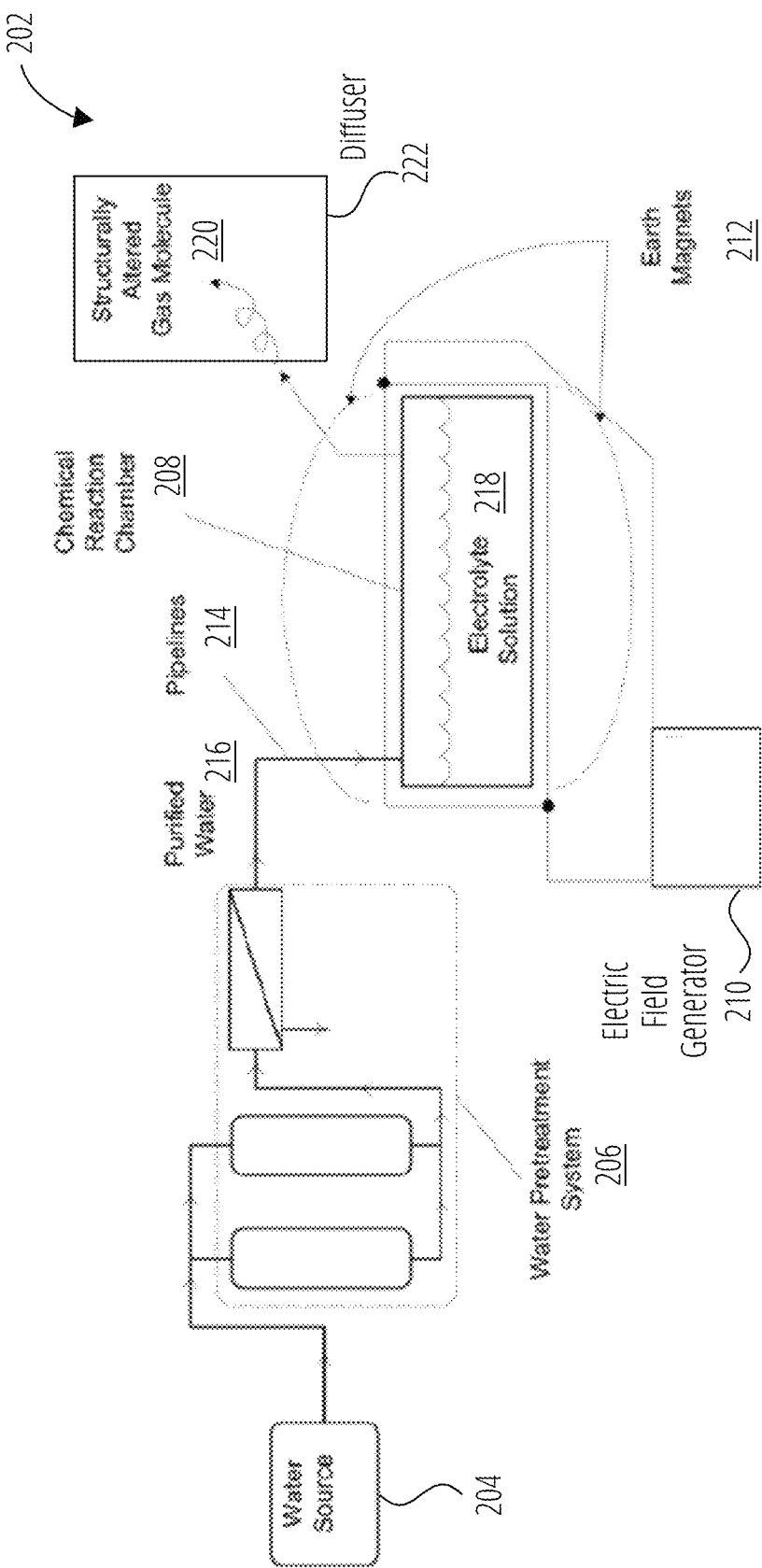
FIG. 2 is a diagram showing a system for enhancing production of ATP in living organisms, according to an example embodiment.

The following detailed description of embodiments includes references to the accompanying drawings, which form a part of the detailed description. Approaches described in this section are not prior art to the claims and are not admitted to be prior art by inclusion in this section. The drawings show illustrations in accordance with example embodiments. These example embodiments, which are also referred to herein as "examples," are described in enough detail to enable those skilled in the art to practice the present subject matter. The embodiments can be combined, other embodiments can be utilized, or structural, logical, and operational changes can be made without departing from the scope of what is claimed. The following detailed description is, therefore, not to be taken in a limiting sense, and the scope is defined by the appended claims and their equivalents.

Generally, the embodiments of this disclosure relate to methods for application of a structurally altered gas molecule to enhance production of ATP in living organisms with no increase in reactive oxygen species. The method of the present disclosure uses conventional water treatment technologies to generate a purified liquid. That liquid is added to a chemical reaction chamber containing an electrolyte solution. This mixture is treated by a focused magnetic field using a magnetic field generator and an electric field to generate an altered, gaseous form of the purified liquid. The generated altered water molecule gas can then be deployed directly or mixed into the liquids that interface with living organisms to enhance their performance and promote ATP production in the living cells that constitute these living organisms. This includes all lifeforms (plants, animals, fungi, mold hyphae) that use ATP as the primary energy source.

The method for deploying a structurally altered gas molecule to enhance the production of ATP in living organisms has been demonstrated with reproducible results. ATP is a molecule that is created by and is a vehicle for carrying energy within living cells. It is the main energy currency of the cell, and it is a product of the primary function of the mitochondria present in all living cells—plant and animal—through a process of photo/oxidative phosphorylation. Photo/oxidative phosphorylation is a biochemical process that involves adding a phosphate group to a molecule using energy from light, and/or cellular respiration, and/or fermentation. All living things use and rely on ATP and a production boost of ATP is meaningful to the healthy functioning of the cell. In addition to being used as an energy source, ATP is also used in signal transduction pathways for cell communication and is incorporated into deoxyribonucleic acid (DNA) during DNA synthesis.

Components involved in the method of the present disclosure include water, water pretreatment equipment, reaction chamber, electrolyte solution, a magnetic field generator, and electricity. Additional components may include pressure regulators, an electrical inverter, solar panels, a gas diffuser for diffusing gas into atmosphere or liquid that living cells can interface with and uptake the altered water molecule in gaseous and/or liquid form.

Water serves as the raw material that the gas product is generated from. The water pretreatment equipment prepares above said water for the reaction chamber (uses conventional filtration, absorption and purification). The reaction chamber provides the reaction vessel that holds the electrolyte solution and the purified water for the magnetic field to chemically convert the purified water into an altered gaseous form of said purified liquid. Electrolyte solution provides the medium for the magnetic field to align and impart its energy on the purified water mixed in with the electrolyte solution to chemically generate the altered gaseous form of said water. In an example embodiment, the magnetic field generator may include one of the following: earth magnets, solenoids, electromagnets, and so forth. The magnetic field generator creates magnetic field to drive the chemical reaction that generates the altered form of the gaseous water.

Once generated, the gas can be deployed directly into the targeted atmosphere or diffused in the liquid that in either case interfaces with the living organisms that can uptake and utilize the gas to increase mitochondrial function, oxidative phosphorylation, and the resulting ATP production. The diffuser may infuse gas to atmosphere or a liquid deployment system to cause the living organisms to interface with and uptake the altered gas molecules.

Conventional water treatment processes typically provide mediocre results. The method of the present disclosure provides the increased ATP production and resulting benefits as described below.

Referring now to the drawings, various embodiments are described in which like reference numerals represent like parts and assemblies throughout the several views. It should be noted that the reference to various embodiments does not limit the scope of the claims attached hereto. Additionally, any examples outlined in this specification are not intended to be limiting and merely set forth some of the many possible embodiments for the appended claims.

This application makes reference to U.S. patent application Ser. No. 17/487,613, filed on Sep. 28, 2021, now U.S. Pat. No. 11,384,440, and to U.S. patent application Ser. No. 17/743,632, filed on May 13, 2022, now U.S. Pat. No. 11,634,823, the subject matter of which is incorporated herein by reference in its entirety for all purposes. Processes and systems described herein may be better understood in light of the concepts found in these references.

FIG. 1 shows a structurally altered gas molecule 102 deployed in the process of the present disclosure. The structurally altered gas molecule deployed in the process of the present disclosure is a structurally altered gas molecule generated by processes described in U.S. Pat. Nos. 11,384,440 and 11,634,823, the subject matter of which is incorporated herein by reference in its entirety for all purposes.

During the alterations, hydrogen bonds 104 are broken to allow a gaseous single molecule form of water to exist and enable the following adjustments: 1) a bond angle 106 is decreased; 2) oxygen-hydrogen covalent bond length 108 is increased; 3) adjustments allow room for more electrons in probability spheres 110. Per the molecular orbital theory (MOT), small molecules like water can adjust electron energy levels around the probability spheres. The MOT states that not just the atoms themselves but the entire molecule shares electrons now.

As for the structurally altered gas molecule 102, the molecular alterations include lengthening of the H—O bonds from 0.95 Angstroms up to 1.3 Angstrom and decreasing the H—O—H bond angle from 104.5° to as small as 94°. These changes alter the chemical properties of the water that the gas may be infused into. These changes include a decrease in normal pure water pH (from 7.0 to ~6.5), and a shift in redox potential from 0 mV to ~−200 mV. This gas has been diffused into normal pure water where it has been demonstrated that the infused gas imparts some of its above-described properties to the un-gassed normal pure water.

The restructuring of liquid un-gassed diffused normal water molecules by diffusion of the structurally altered gas molecules 102 into the normal un-gassed diffused liquid water has provided a number of observed alterations in the gas diffused water. The first alteration is reduction in intermolecular hydrogen bonding between water molecules in liquid phase. Hydrogen bonding in water is a dynamic attraction between positively charged hydrogen atoms of one water molecule and negatively charged oxygen atoms of another water molecule. This occurs because of the difference in electronegativity between hydrogen and oxygen atoms.

The second alteration is reduction in the dipole moment of the gas treated water. The dipole moment is a measure of the separation of positive and negative electrical charges within a system. Water has a dipole moment because water has a bent structure and the electronegativity difference between atoms of oxygen and hydrogen.

The third alteration is reduction in the ion-dipole force formed between ions and water. The ion-dipole force is a force of attraction between an ion and a neutral molecule that has a dipole.

These alterations reduce the tendency of the water molecules to "clump" through hydrogen bonding, and its dipole moment. The alterations also provide a reduction in the ion-dipole force formed between ions and water to facilitate the separation and passage of individual water molecules through ion water separation technologies used in the separation of ions (both soluble and insoluble) from process fluids and in the purification of water. With these changes provided by the structurally altering gas molecules, the desirable effects on the chemical kinetics (speed of reaction) and thermodynamics (how far to completion the reactions may go) have been demonstrated.

The gas can be deployed directly into the intended space or diffused into liquid that, in either case, interfaces with the living organism in said space. Living organisms can then uptake and utilize the gas to increase mitochondrial function, increase oxidative phosphorylation, and enhance resulting ATP production, with and the attendant benefits therefrom.

FIG. 2 is a diagram showing an example system 202 for generating a structurally altered gas molecule and enhancing production of adenosine triphosphate (ATP) in living organisms, according to an example embodiment. The system 202 may include a water source 204, a water pretreatment system 206, a chemical reaction chamber 208, an electric field generator 210, a magnetic field generator, e.g., in the form of earth magnets 212, a diffuser 222, and pipelines 214. The system 202 may also include pressure regulators. The electric field generator 210 may include an electrical inverter and solar panels.

The water source 204 may provide water as a raw material for generating the gas molecule product. The water pretreatment system 206 may prepare the water for the chemical reaction chamber 208. The water pretreatment system 206 may include a filtration system, an absorption system, and a purification system to produce the purified water 216.

The chemical reaction chamber 208 may contain an electrolyte solution 218. The electrolyte solution 218 can be made using a mixture of a hydroxide salt and an acid salt. The purified water 216 can be provided to the chemical reaction chamber 208. The earth magnets 212 may generate a permanent focused magnetic field. The electric field generator 210 may generate an electric field. The focused magnetic field and the electrical field may drive chemical reaction that generates the structurally altered gas molecule 220 from the purified water supplied into the chemical reaction chamber 108. The electrolyte solution 218 may provide a medium for the focused magnetic field to align and impart energy of the focused magnetic field on the purified water mixed in with the electrolyte solution and, thereby, chemically generate the structurally altered gas molecule 220 from the purified water 216. The temperature in the chemical reaction chamber 208 can be from 60 degrees to 120 degrees Fahrenheit. The pressure in the chemical reaction chamber 208 can be from 1 atmosphere to 40 pounds per square inch gauge (psig).

In the system 202, the magnetic field generator (e.g., the earth magnets 212) and the electric field generator 210 are configured to apply the magnetic field and the electric field to water to cause generation of structurally altered gas molecules from the water. The structurally altered gas molecules have a higher probability of attraction of electrons into areas adjunct to the structurally altered gas molecules than molecules of the water. The diffuser 222 may be configured to infuse the structurally altered gas molecules into a living organism. In an example embodiment, the diffuser 222 is a gas diffuser for diffusing gas into atmosphere or liquid that living organisms can interface with and uptake the altered water molecule in gaseous and/or liquid form. Upon being infused, the structurally altered gas molecules cause an increase of production of the ATP in the living organism.

The structurally altered gas molecule 220 can be 99.9% hydrogen and oxygen combination in two parts of hydrogen to one part of oxygen ratio at the standard temperature of 68 degrees Fahrenheit and pressure of 1 atmosphere (STP). The structurally altered gas molecule 220 may have the O—H bond length between 0.95 and 1.3 angstroms and the H—O—H bond angle between 94 degrees and 104 degrees.

The molecular weight of the structurally altered gas molecule 220 can be between 12.14 and 12.18 atomic mass units (AMUs) at STP. In comparison, the molecular weight of pure water vapor is 18 AMUs at STP. At STP, the relative density of the structurally altered gas molecule 220 compared to dry air is 41.18%-42.00%. In comparison, relative density of pure water vapor compared to dry air is 62.19%. The structurally altered gas molecule 220 may remain stable at pressure more than 300 psig.

When dissolved in pure water having 2 parts per million (ppm) of total dissolved solids (TDS) at 25 degrees of Celsius, the structurally altered gas molecule 220 may generate an oxidation reduction potential (ORP) of approximately −50 to −360 mV and a pH of 6.1 to 6.8 in the resulting gas-water mixture. The ORP and pH may remain stable in a closed insoluble vessel for at least 30 days. In comparison, the pure water does not possess a stable negative ORP at a pH below 7.

When dissolved in pure water (2 ppm TDS at 25 degrees Celsius), the structurally altered gas molecule 220 may reduce the concentration of TDS from 2.0 ppm to 1.0 ppm, i.e., the reduction is 50%. Barring contamination, the concentration of TDS remains stable at 1 ppm in a closed insoluble vessel indefinitely.

The changes in structure and properties of the structurally altered gas molecule 220 are caused by changes in electronic structure of the gas structurally altered structurally altered gas molecule 2200 due to applying the focused magnetic field and the electrical field to the mixture of the electrolyte solution 218 and purified water 216.

In an example embodiment, a structurally altered gas molecule 220 used in the method for enhancing production of ATP in living organisms is a combination of two parts of hydrogen and one part of oxygen and produced from water. The structurally altered gas molecule 220 is produced by placing an electrolyte solution in a chemical reaction chamber, adding purified water to the chemical reaction chamber, and applying a focused magnetic field generated by a magnetic field generator and an electric field to a mixture of the purified water and the electrolyte solution to cause generation of the structurally altered gas molecule from the purified water. The temperature in the chemical reaction chamber may be from 60 degrees to 120 degrees Fahrenheit. The pressure in the chemical reaction chamber may be from 1 atmosphere to 40 psig. The structurally altered gas molecule 220 has a hydrogen-oxygen-hydrogen bond angles between 94 degrees and 104 degrees and hydrogen-oxygen bond length between 0.95 Angstrom and 1.3 Angstrom. A hydrogen bonding of the structurally altered gas molecule 220 is neutralized. The structurally altered gas molecule 220, when being dissolved in water, may have two parts per million (ppm) of TDS, causing the TDS to reduce to one ppm. When being dissolved in the purified water, the structurally altered gas molecule 220 and the water may form a solution having a pH ranging from 6.1 to 6.8.

The structurally altered gas molecule 220 may be produced with a mixture of a hydroxide salt and an acid salt as the electrolyte. The structurally altered gas molecule 220 may have a density relative to a dry air of from 41.18% to 42%. The structurally altered gas molecule 220 may be stable at a pressure exceeding 300 psig. The structurally altered gas molecule 220 may have a peak at 600 inverse centimeters in an infrared spectrum.

In an example embodiment, upon dissolving the structurally altered gas molecule 220 in water, a solution of the structurally altered gas molecule 220 and water is produced. The solution may have an oxidation/reduction potential of −50 to −360 millivolts and pH from 6.1 to 6.8. The oxidation/reduction potential and the pH may remain stable for at least 30 days after the solution is placed in a closed insoluble vessel. When infused in water, the structurally altered gas molecule 220 may cause a hydrogen bonding in the water to be neutralized.

Figure 3:
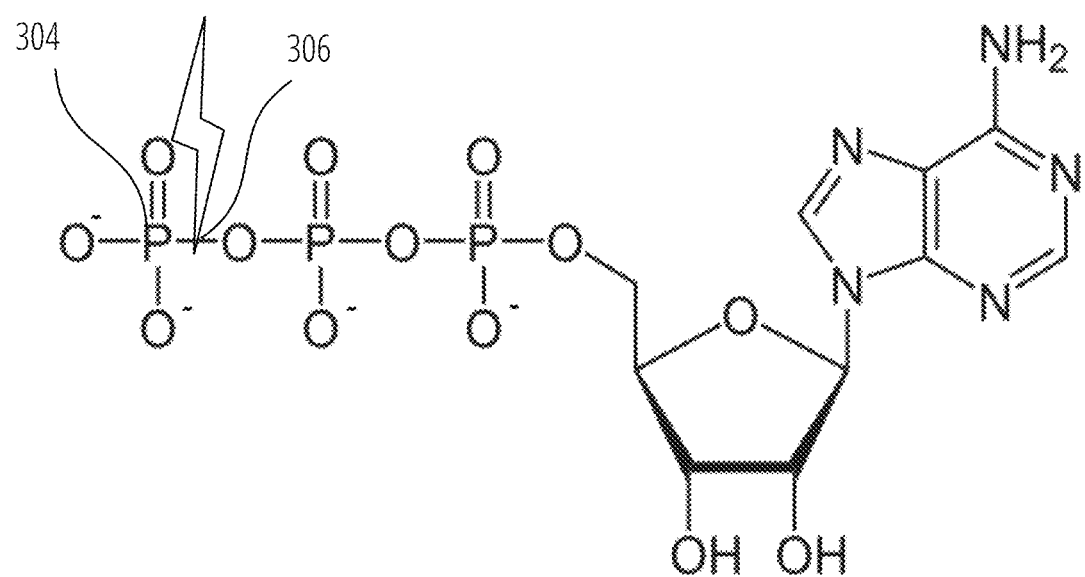
FIG. 3 shows a structure of an ATP molecule.

FIG. 3 shows a structure 302 of an ATP molecule. FIG. 3 shows a terminal phosphate group 304 that releases energy when a high energy bond 306 is broken.

Increasing ATP production in living cells. Other than the conventional methods cited below (for humans), at present there are no known processes or systems that produce a broad-based increase in ATP production in living cells.

The following conventions are focused on selling concepts and consumables to humans, the claims of potential ATP production and the drawback if these practices are not part of a health regiment.

Calorie restriction. Calorie restriction acts as a stress signal that triggers a number of adaptations in mitochondria: it improves the activity of the electron transport chain and regulates the production of reactive oxygen species (ROS) and oxidative stress; it supports mitochondrial quality control mechanisms, responsible for preventing and/or repairing damage; it also promotes the renewal of the mitochondrial network through the elimination of damaged mitochondria (autophagy) and the production of new mitochondria (biogenesis).

Exercise. Exercise requires a great deal of energy to power our muscles. That puts a burden on muscle mitochondria, which signals that energetic demand to the rest of the cell.

Muscle cells respond by producing more mitochondria and more mitochondrial enzymes. This increases the respiratory capacity of muscles, i.e., their ability to produce ATP from nutrients to power muscle contraction.

It is an adaptation of our muscle cells to exercise and one of the reasons why exercise performance improves with training. Exercise is also one of the best ways to improve mitochondrial biogenesis and function in aging muscle, helping delay the age-related decline in mitochondrial activity and muscle health.

Nutrients. There are many nutrients that can help mitochondria do their work and maintain their fitness. Mitochondrial nutrients provide substrates and cofactors that support and/or stimulate mitochondrial enzyme activity, they enhance cellular antioxidant defenses, they scavenge free radicals and protect mitochondria from oxidation, and they protect and repair mitochondrial membranes.

Mitochondrial nutrients include B vitamins, minerals, polyphenols and other nutrients, such as L-carnitine, alpha-lipoic acid, coenzyme Q10, pyrroloquinoline quinone and creatine, for example. They can be taken as supplements, or they can be found in natural, unprocessed foods, i.e., fruits and vegetables, nuts and seeds, seafood, and meat.

Rest. The human brain requires a lot of energy, and because of its high metabolic rate, the brain accumulates a lot of metabolic waste. During sleep, the brain gets rid of products that can be toxic to mitochondria.

An example is the molecule beta-amyloid. At normal levels, beta-amyloid protects neurons and supports their activity. However, when it accumulates excessively, beta-amyloid becomes harmful to neurons, in particular to their mitochondria, which can trigger neurodegenerative processes. Because neuronal mitochondria powers functioning brain, it is very important to avoid this accumulation of toxic waste which may damage mitochondria.

Consuming NAD+ from nicotinamide adenine dinucleotide (NAD). NAD+ is a molecule derived from vitamin B3 found in every single cell in the body. $NAD^+$ has a key role in mitochondrial function: it is the main molecule responsible for the delivery of the electrons that are extracted from food to the electron transport chain for ATP production. $NAD^+$ is therefore as important for cells as ATP itself. Consequently, $NAD^+$ is essential for the maintenance of health. $NAD^+$ levels decrease naturally in many tissues with age. This decrease may also contribute to the aging process.

Although some athletes may slightly improve their performance by taking supplements or ergonomic aids designed to increase ATP production, it is debatable that oral ATP supplementation actually increases energy.

Dysfunctions in the mechanisms of ATP production in mitochondria, particularly in a pathway called the electron transport chain, increase the production of byproducts called ROS that can be damaging to mitochondria at high concentrations. Mitochondrial dysfunction creates a rolling snowball of damage that can gradually grow to affect all biological processes.

This happens naturally with age of the organism, but improving mitochondrial health, their efficacy in generating energy, and their capacity to avoid or repair damage to their biochemical machinery may contribute to a healthier aging process.

It should be noted here that the process of the present disclosure provides an abundance of electrons for the above-described electron transport chain, (per U.S. Pat. No. 11,384,440 and U.S. Pat. No. 11,634,823). It should also be noted here that in the first experiment listed below, where the only variable was introduction of the process of the present disclosure, resulted in a 25% increase in ATP production and a trend towards a decrease in hydrogen peroxide ROS production during respiration supported by Complex II (0.00106 vs 0.00202 nmol $H_2O_2$/pmol $O_2$, p=0.089).

Decreased mitochondrial ATP-production are common findings during critical illness and considered to be associated with decreased activity of muscle mitochondrial complexes in the electron transfer system. Adequate nutrient levels are essential for mitochondrial function as several specific micronutrients play crucial roles in energy metabolism and ATP production.

Most of the ATP synthesized during glucose metabolism is produced in the mitochondria through oxidative phosphorylation. This is a complex reaction powered by the proton gradient across the mitochondrial inner membrane, which is generated by mitochondrial respiration.

Chemiosmosis, a process of ATP production in cellular metabolism, is used to generate 90 percent of the ATP made during glucose catabolism and is also the method used in the light reactions of photosynthesis to harness the energy of sunlight. The production of ATP using the process of chemiosmosis is called oxidative phosphorylation because of the involvement of oxygen in the process.

Five experiments were conducted by using the process of the present disclosure. In all experiments, the only variable introduced was the testing with and without the presence of the structurally altered gas molecule.

The first experiment relates to application of a structurally altered gas molecule to enhance production of ATP in living organisms. The experiment is directed to ex vivo testing of the water infused with structurally altered gas molecules on skeletal muscle mitochondrial function.

Data and conclusions. The maximal rate of ATP synthesis was significantly increased by 25% through incubation of mitochondria in water infused with the altered gas molecule compared to standard ultrafiltered laboratory water, with all other parameters and effects equalized (419.65 vs 335.43 pmol ATP/(s*ml), p=0.005).

Incubation of freshly harvested skeletal muscle mitochondria in the altered gas-produced water resulted in a 13% increase in maximal rates of phosphorylating respiration compared to standard ultrafiltered laboratory water (134.4 vs 119.1 pmol $O_2$/(s*ml), p=0.0653). This effect was driven primarily by an effect on Complex II-based respiration, which was increased by 21% (85.67 vs 70.66 pmol $O_2$/(s*ml), p=0.0285). In contrast, respiration supported by Complex I was not significantly affected (80.64 vs 76.07 pmol $O_2$/(s*ml), p=0.4501). Incubation of mitochondria in the altered gas produced water resulted in a significant increase in calculated mitochondrial efficiency compared to standard ultrafiltered laboratory water (96.50 vs 96.05%, p=0.0416). This increase in efficiency was the result of the increase in maximal phosphorylating respiration, as there was no effect of water source on leak respiration (4.444 vs 4.505 pmol $O_2$/(s*ml), p=0.6667) or leak respiration flux control ratio (6.467 vs 6.679%, p=0.6909). There was a trend towards a decrease in hydrogen peroxide ROS production during respiration supported by Complex II (0.00106 vs 0.00202 nmol $H_2O_2$/pmol $O_2$, p=0.089).

The second experiment relates to application of a structurally altered gas molecule to enhance production of ATP in living organisms, namely live thoroughbred horses. The experiment is directed to evaluation of exercise performance in response to ingestion of water infused with the altered gas molecule in horses. The objective of this experiment was to assess the effect of saturation of body water with the altered gas-produced water on exercise performance in fit thoroughbred horses completing: (1) a stepwise treadmill exercise test to determine maximum oxygen consumption ($VO_2$max), and (2) a run to fatigue at a fixed submaximal exercise intensity ($VO_2$=75-80% $VO_2$max). The point of fatigue was deemed to have been reached when horses could no longer maintain the speed of the treadmill despite verbal encouragement.

Data. Blood work on horses. FIG. 4 shows a table 402 of blood test results of horses. There was no sign of any hematological or serum biochemical abnormality associated with the consumption of water infused with the altered gas molecule for 21 days. The horses' water consumption was also normal and ranged from 10-16 gallons/day.

Figures 5A, 5B:
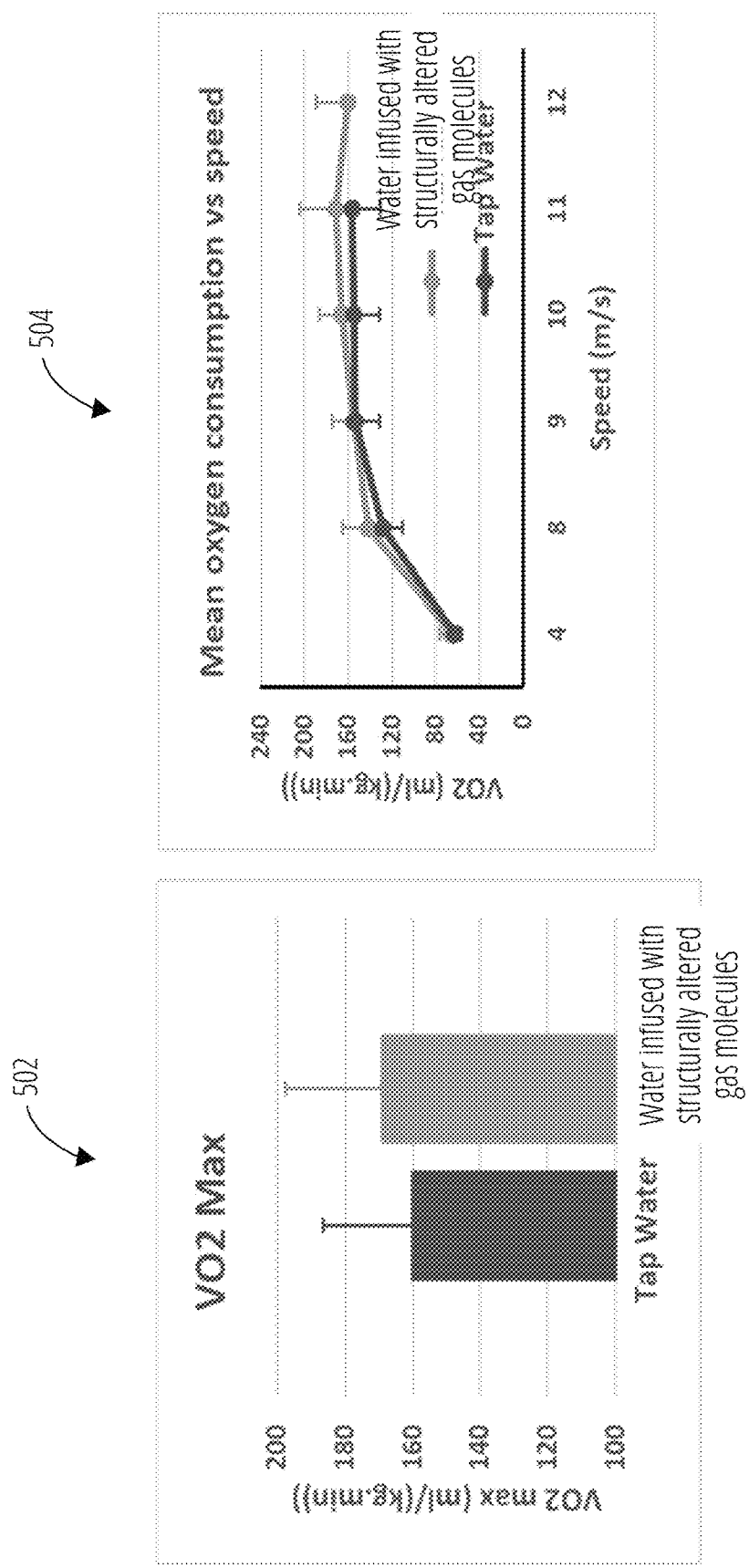
FIG. 5A shows a diagram illustrating maximal oxygen consumption, according to an example embodiment.
FIG. 5B shows a diagram illustrating mean oxygen consumption vs speed, according to an example embodiment.

FIG. 5A shows a diagram 502 illustrating maximal oxygen consumption ($VO_2$max). The data from one horse had to be deleted due to a technical error during one of the treadmill runs. For n=7, the p value approached significance (p=0.06, FIG. 5A). This may be interpreted as meaning that there was a 94% certainty that drinking water infused with the altered gas molecule increased $VO_2$max.

FIG. 5B shows a diagram 504 illustrating mean oxygen consumption vs speed. It was also notable that 4 of the horses were able to run at 12 m/s (26.8 mph at 8% incline) after drinking the water infused with the altered gas molecule (H) while only one of the control (tap water, (T)) horses reached this speed, and could only maintain it for 20 sec (FIG. 5B). The speed at which $VO_2$max was reached however, was not different for the two treadmill tests (9.9±0.7 m/s (T) vs 9.8±1.1 m/s (H); p=0.79). This suggested that the percentage of total energy being produced by aerobic means was higher following ingestion of than after drinking tap water, given the higher $VO_2$max at these points. This is of relevance in terms of performance because the lower the anaerobic contribution to total energy production, the longer the horse can run at its $VO_2$max all other things remaining the same. Or, put another way, the further or longer it can run at a given speed until fatigue sets in.

The horses' health was not adversely affected by drinking the water infused with structurally altered gas molecules. There were no detectable changes in their blood profiles and there was no change in their daily water consumption. The horses were fit when they began the experiment and there was no apparent improvement or decrease in their aerobic capacity over the course of the experiment. Despite this, their $VO_2$max was increased (94% probability) and their endurance was enhanced as reflected by the marked increase in the run time to fatigue in 7 of the 8 horses. These findings are compatible with and affirm the ex-vivo finding that mitochondrial ATP synthesis was enhanced in the presence of water infused with structurally altered gas molecules. The reason for the improvement in stamina also may be that the saturation of the body with re-structured water infused with structurally altered gas molecules may have been associated with a reduction in the presence and/or effect of oxidants like ROS in the muscles. Reduced production of ROS in the long head of the triceps following consumption of water infused with structurally altered gas molecules is compatible with an increase in the efficiency of ATP production due to the finished structure of water infused with structurally altered gas molecules representing that of intracellular water.

Figures 6A, 6B:
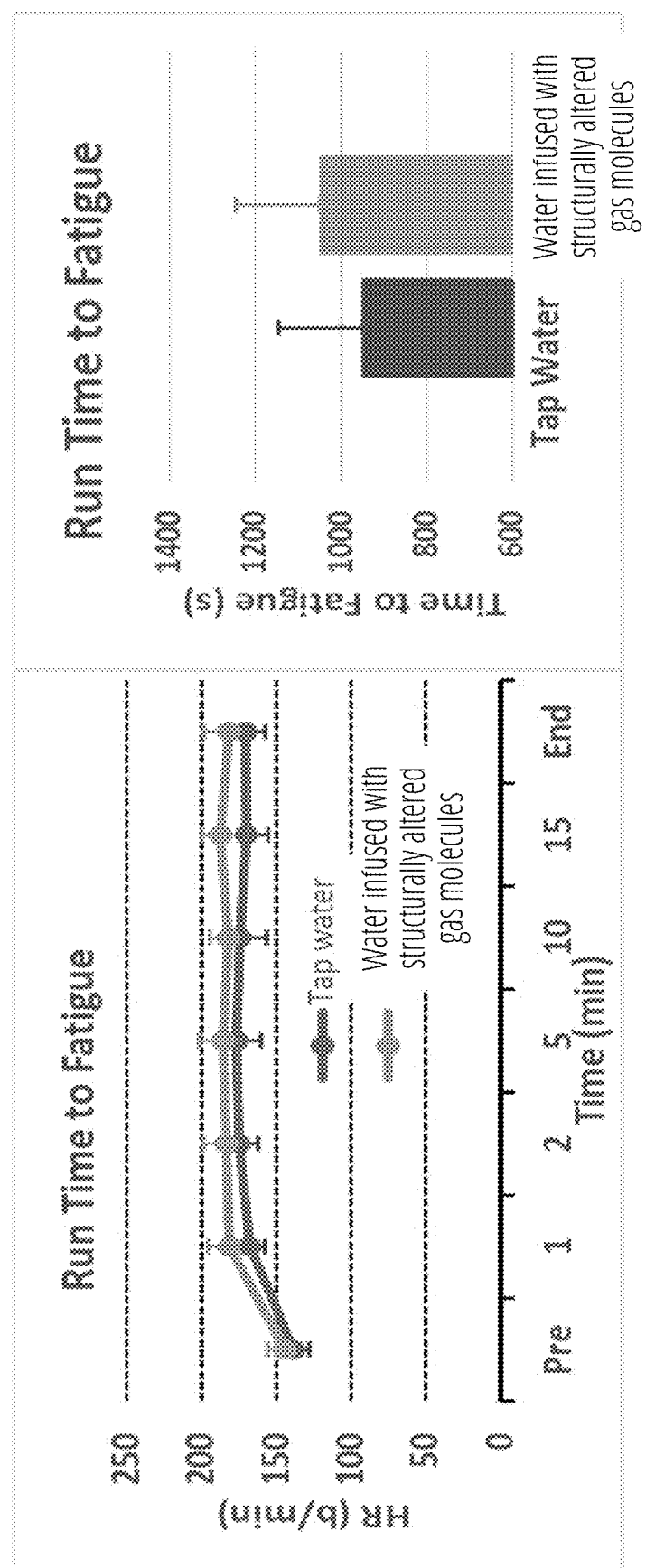
FIG. 6A illustrates run time to fatigue, according to an example embodiment.
FIG. 6B illustrates run time to fatigue, according to an example embodiment.

FIG. 6A and FIG. 6B illustrate run time to fatigue. Seven of the 8 horses ran longer after drinking water infused with structurally altered gas molecules. Three horses failed to run for 15 mins in the control run and one of them also failed to run 15 mins after drinking water infused with structurally altered gas molecules although the latter run was about 2 min 45 s longer. All other horses ran >15 min after drinking water infused with structurally altered gas molecules. The difference in the run time to fatigue approached significance (p=0.07). One horse ran longer in the control (T) run (there was a cooler ambient temperature that day) and if its data are deleted (n=7, p=0.02), the horses ran more than 2 mins longer with water infused with structurally altered gas molecules (908±182 sec (T); 1047±232 sec (H); see FIG. 6A, FIG. 6B).

The relative intensity at which these tests were completed did not differ (77.8±13.2% VO$_2$max (T) vs 77.3±9.9% VO$_2$max (H), p=0.99). The fact that these intensities were not different between the two tests was reassuring, as it was important that they completed each test at the same intensity as the most supportable conclusion is that the same horses displayed more stamina after drinking water infused with structurally altered gas molecules.

Conclusions. The horses' health was not adversely affected by drinking the water infused with structurally altered gas molecule. There were no detectable changes in their blood profiles and there was no change in their daily water consumption. The horses were fit when they began the experiment and there was no apparent improvement or decrease in their aerobic capacity over the course of the experiment. Despite this, their VO$_2$max was increased (94% probability) and their endurance was enhanced as reflected by the marked increase in the run time to fatigue in 7 of the 8 horses. These findings are compatible with and affirm the ex-vivo finding that mitochondrial ATP synthesis was enhanced in the presence of water infused with structurally altered gas molecules. The reason for the improvement in stamina also may be that the saturation of the body with re-structured water infused with structurally altered gas molecules may have been associated with a reduction in the presence and/or effect of oxidants like ROS in the muscles. Reduced production of ROS in the long head of the triceps following the consumption of water infused with structurally altered gas molecules is compatible with an increase in the efficiency of ATP production due to the finished structure of water infused with structurally altered gas molecules representing that of intracellular water.

The third experiment relates to application of a structurally altered gas molecule to enhance production of ATP in living organisms, namely chickens. The third experiment is directed to effect of water infused with structurally altered gas molecules on growth and feed efficiency of broiler hens.

Figure 7:
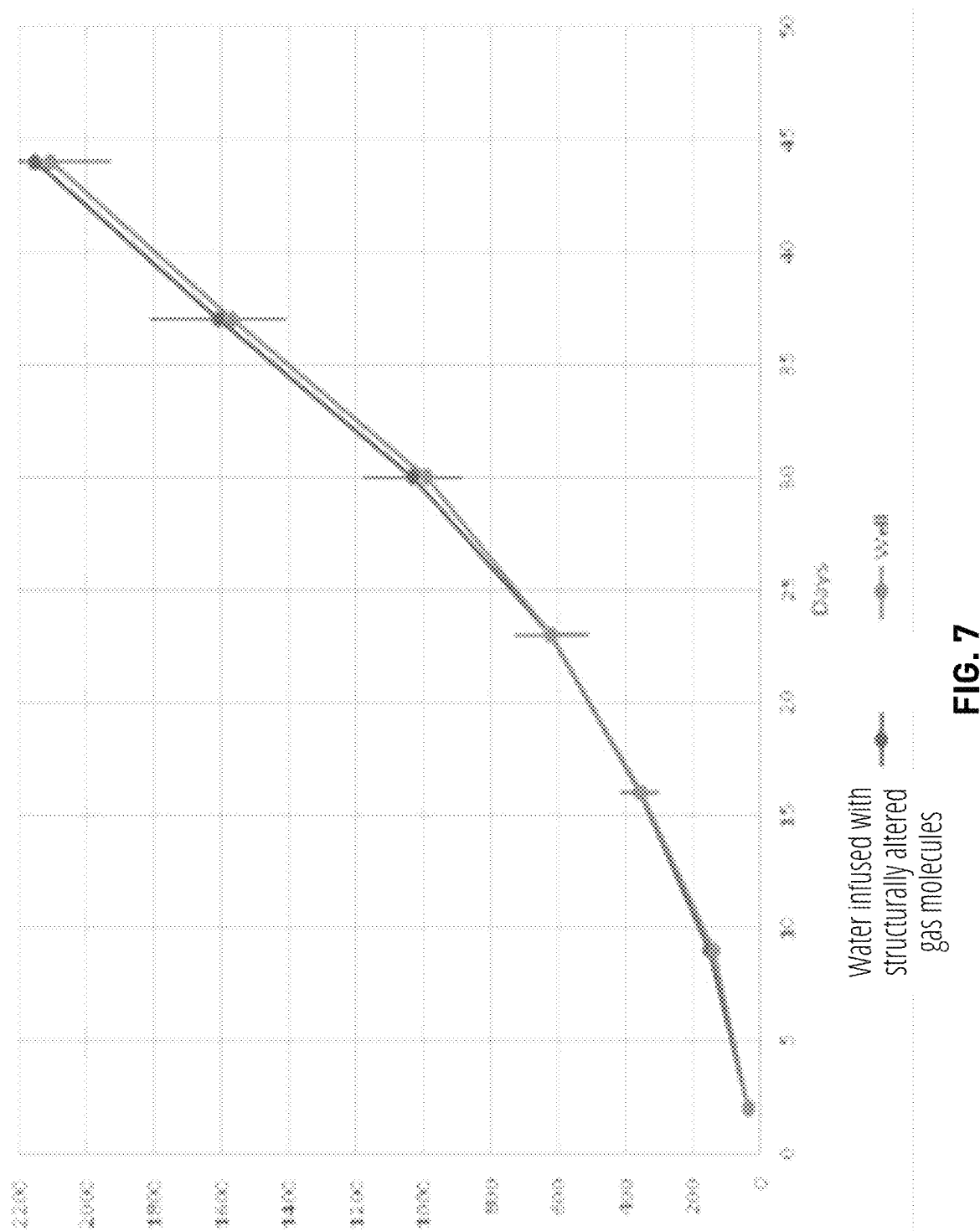
FIG. 7 shows broiler hen average weight in grams vs time for broiler hens that drank water infused with structurally altered gas molecules vs broiler hens that drank well water, according to an example embodiment.

FIG. 7 shows broiler hen average weight in grams vs time (days) for broiler hens that drank water infused with structurally altered gas molecules vs broiler hens that drank well water. The results of this experiment provide support for the conclusion that water infused with structurally altered gas molecules is safe for animals during periods of rapid growth when they are most susceptible to growth-related abnormalities.

The sole subjective difference found between the two groups during postmortem evaluation was an increase in visceral fat mass in the chickens raised on water infused with structurally altered gas molecules. It is possible that this difference is secondary to the ability of water infused with structurally altered gas molecules to increase mitochondrial function and the availability of cellular energy, thus allowing the chickens to be raised in a metabolic state of surplus energy. The chickens raised on water infused with structurally altered gas molecules were slightly larger than the Control chickens.

The fourth experiment relates to application of a structurally altered gas molecule to enhance production of ATP in living organisms, namely plants. The experiment is directed to the effect of water infused with structurally altered gas molecules on growth of tomatoes.

Figure 8:
FIG. 8 shows a plant watered with water infused with structurally altered gas molecules, a plant watered with reverse osmosis water, and a plant watered with tap water, according to an example embodiment.
Figure 9:
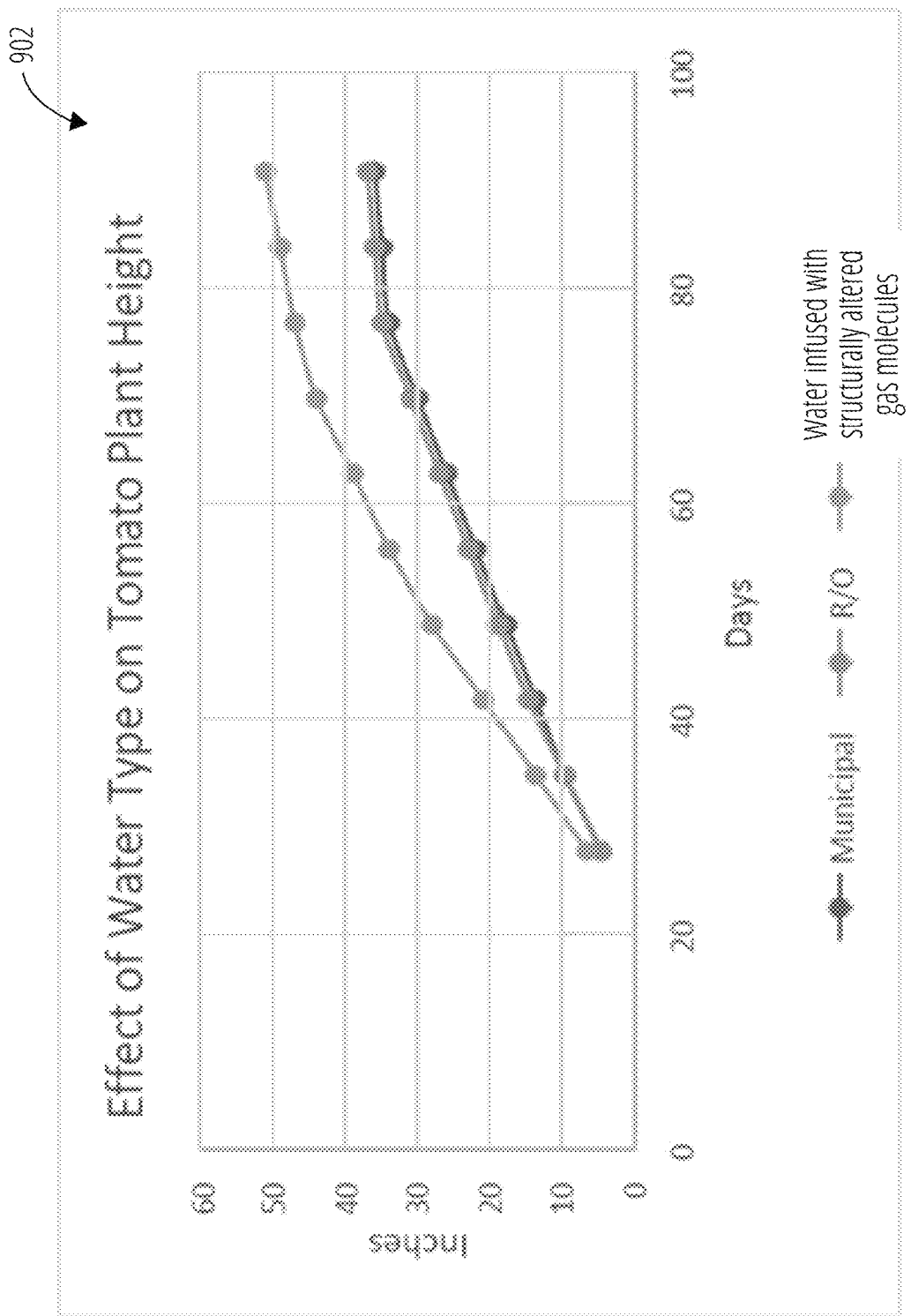
FIG. 9 is a diagram illustrating effect of water type on height of the tomatoes plants, according to an example embodiment.

The results of the fourth experiment are shown in FIG. 8 and FIG. 9. FIG. 8 shows a plant 802 watered with water infused with structurally altered gas molecules, a plant 804 watered with reverse osmosis (RO) water, and a plant 806 watered with tap water.

FIG. 9 is a diagram 902 illustrating effect of water type on height of the tomatoes plants. FIG. 9 shows growth of Roma tomato plants irrigated with either municipal tap water, RO water, or water infused with structurally altered gas molecules.

Data expressed as mean±standard deviation. Water infused with structurally altered gas molecules produced 100% seed germination by day 4; by comparison, seeds germinated slower and less completely in tap water and RO water (80% and 90% by day 7, respectively). At day 30 when the plants were transferred to the large grow bags there was a subjective difference in root density, with noticeably denser root cluster in the plants irrigated with water infused with structurally altered gas molecules (see FIG. 8).

Initial fruit formation occurred at 63, 70, and 77 days on plants irrigated with water infused with structurally altered gas molecules, RO water, and tap water, respectively (see FIG. 9). Plants irrigated with water infused with structurally altered gas molecules were taller (129.54 cm) than tap water- and RO-irrigated plants (91.44 and 93.98 cm, respectively) (FIG. 9). At approximately day 80, plants irrigated with water infused with structurally altered gas molecules were requiring water more frequently (every 2 days) compared to RO-irrigated plants (every 3 days) and municipal tap water-irrigated plants (very 4 days).

Figure 10:
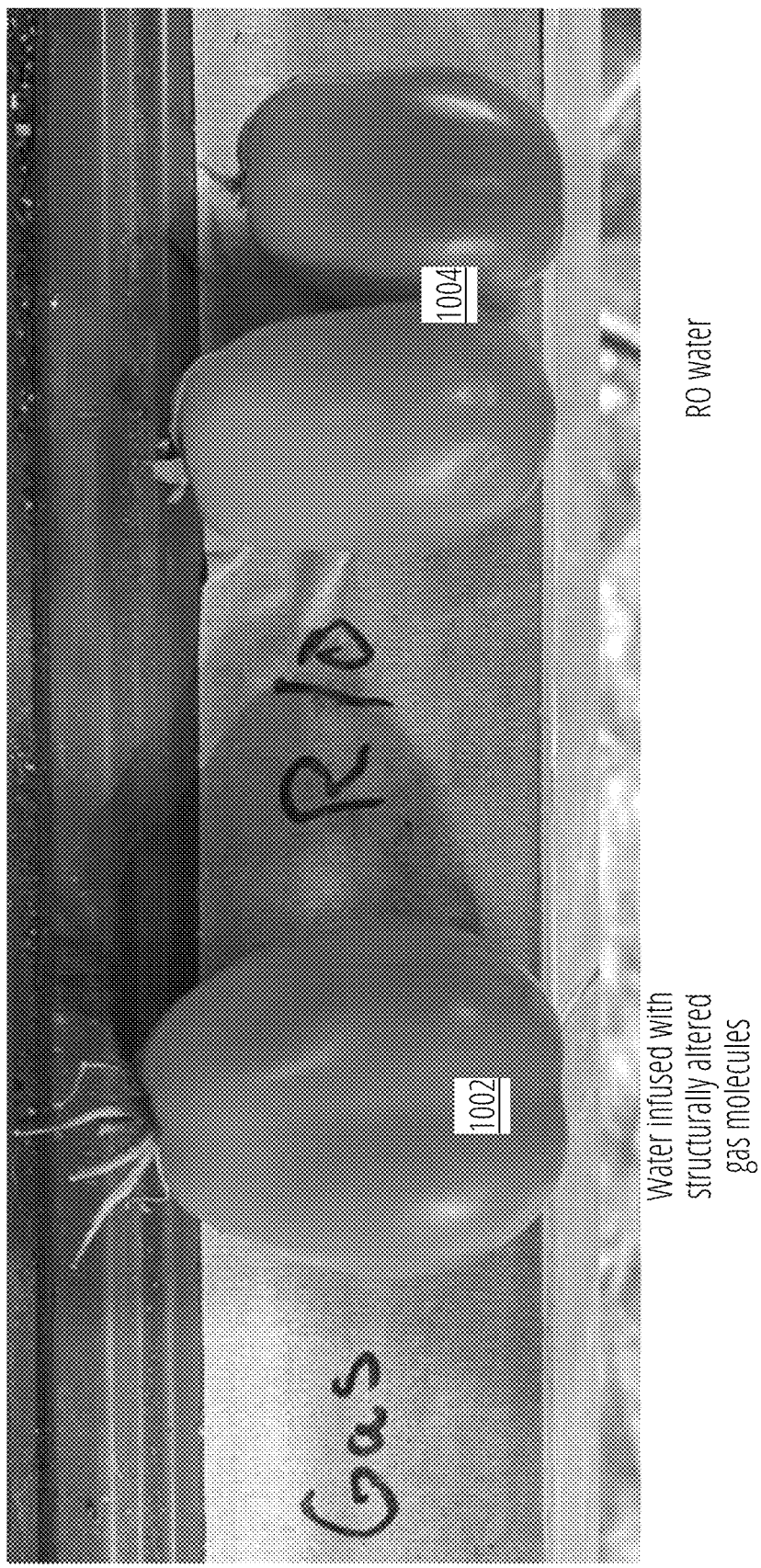
FIG. 10 shows an example of Roma tomato fruit differences depending on the type of water used for irrigation, according to an example embodiment.

FIG. 10 shows an example of Roma tomato fruit differences depending on the type of water used for irrigation. FIG. 10 shows a tomato 1002 irrigated with water infused with structurally altered gas molecules on left and tomatoes 1004 1004 irrigated with RO water on right. There was a significant effect of water source on tomato fruit size (p<0.001), with fruits produced by plants irrigated with water infused with structurally altered gas molecules (90.00±8.897 gm) significantly larger than fruits grown on RO irrigated water (50.00±3.960, p<0.0001) or tap water (40.00±4.255, p<0.0001).

Water infused with structurally altered gas molecules was associated with more complete and faster germination of seeds, faster growth and more root development, and faster production of heavier Roma tomatoes compared to RO water or untreated municipal tap water. With a combination of 25% more complete germination, 22% faster production of fruit, and 125% larger fruit production, water infused with structurally altered gas molecules provided a collective improvement of in Roma tomato production of nearly 350%.

The fifth experiment relates to application of a structurally altered gas molecule to enhance production of ATP in living organisms, namely, aquaponics—plants—fish. The fifth experiment is directed to effect of water infused with structurally altered gas molecules in an aquaponics lettuce grow.

Introduction. A gaseous form of water infused with structurally altered gas molecules is infused into an aquaculture greenhouse lettuce grow. Tilapia (fish) grown in 4×500-gallon tanks are producing nitrate enriched water through denitrification to produce lettuce. Weekly harvests are weighed and packaged for retail sales.

Procedure: Weekly seeding occurs after every harvest. Description of seeds references 55 days till maturity. The process of the present disclosure includes infusing the gaseous form of water into the above-referenced aquaponics system for 10 hours during the daily growing period. The water is being tested and recorded daily for nitrite, nitrate, ammonium, Ph, TDS, temperature, dissolved oxygen (DO) and ORP. The aquaponics system is a gravity feed system running from one trough front to back and then fed into the back of another trough back to the front back to the sump. From the sump water is transferred to the fish tanks through a bacterial filter. The sump water is also transferred to the nursery trough and the germination trays. Solenoids open hourly for 10 minutes during daylight cycle in germination trays (ebb and flow). The nursery trough holds floating lattice in a 12" bed of water. The troughs hold 28 plant count styrofoam floats. 36 floats are harvested and reseeded each week (1008 plants).

FIG. 11 shows a table 1102 illustrating average grams per plant, a seed date, and grams per plant per total days of growth.

Figure 12:
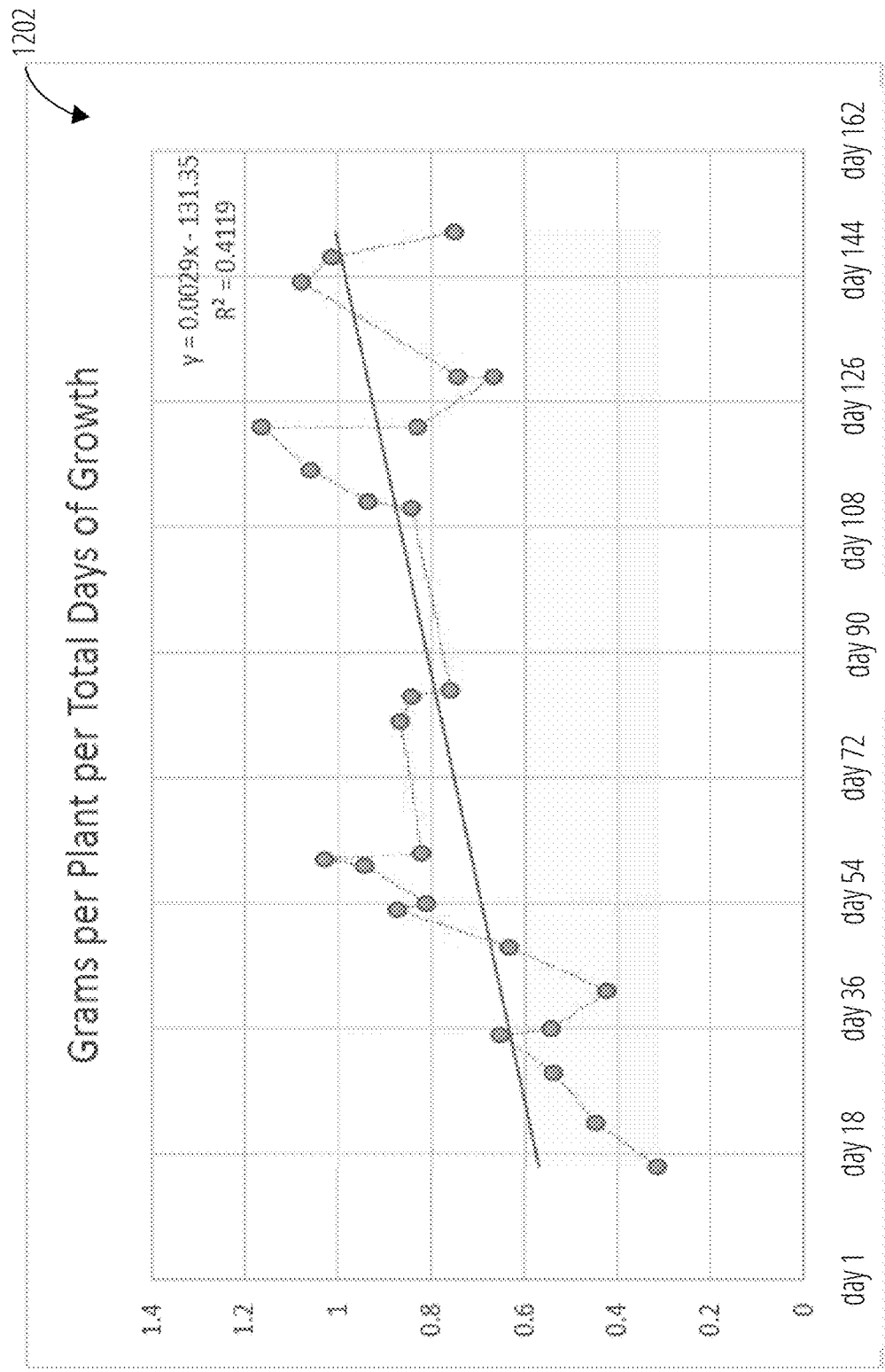
FIG. 12 is a diagram illustrating grams per plant per total days of growth, according to an example embodiment.

FIG. 12 is a diagram 1202 illustrating grams per plant per total days of growth.

After 30 days using the process of the present disclosure, the ORP started to register a consistent negative value. ORP is a measurement used to provide subjective availability of electrons in solution. Ph 6.8, TDS 212, Temp. 74, DO 2%, Ammonium 0.25 ppm, Nitrate vary 2 ppm-10 ppm, Nitrite 0 ppm maintained throughout trial. Fish fed 2× daily with 16 cups between the 4 tanks. Air stones throughout the entire system.

Results. The first 4 harvests of the trial plants were harvested in 12 weeks from seed with an average of 50 pounds per harvest. By week 5 harvest 50 pounds were completed from seed to harvest in 10 weeks. Week 15 into the trial 167 pounds was harvested at 10 weeks from seed to harvest. Week 21 into the trial 121 pounds was harvested at 7 weeks. The average grams per plant per total days of growth increased by 40%.

Conclusions. The average grams per plant per total days of growth increased by 40% with the addition of gaseous form of water infused with structurally altered gas molecules. These results equate to an increase in harvest weights, with a decrease in seed to harvest timing that includes a faster germination time. Also noted was an increase in total root growth, an increase in leaf density and thickness and a better flavor of product.

Figure 13:
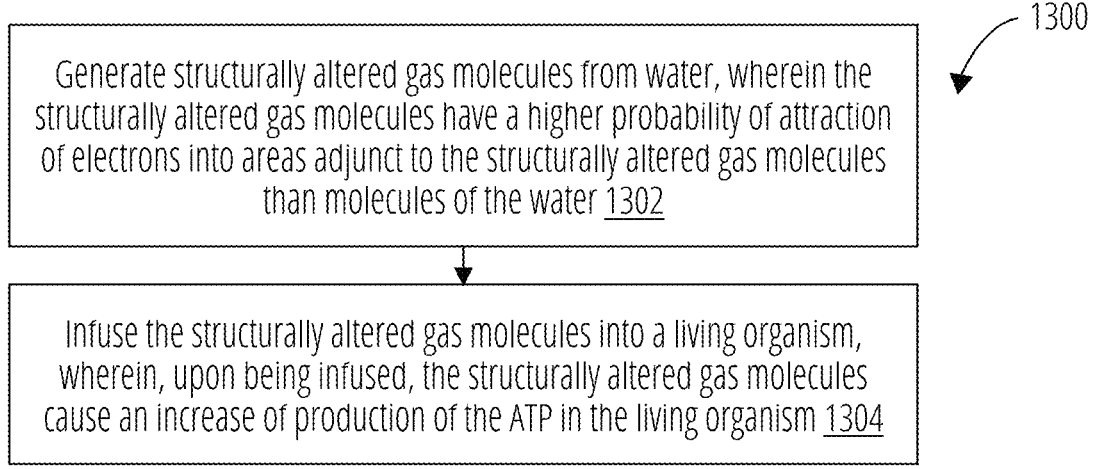
FIG. 13 illustrates a method for enhancing production of ATP in living organisms, according to an example embodiment.

FIG. 13 is a flow chart of a method 1300 for enhancing production of ATP in living organisms, according to an example embodiment. In some embodiments, the operations of the method 1300 may be combined, performed in parallel, or performed in a different order. The method 1300 may also include additional or fewer operations than those illustrated.

In block 1302, the method 1300 may commence with generating structurally altered gas molecules from water. The structurally altered gas molecules have a higher probability of attraction of electrons into areas adjunct to the structurally altered gas molecules than molecules of the water.

In an example embodiment, the generation of structurally altered gas molecules may include placing an electrolyte solution in a chemical reaction chamber, adding purified water to the chemical reaction chamber, applying a focused magnetic field and an electric field to a mixture of the purified water and the electrolyte solution to cause generation of the structurally altered gas molecule from the purified water. The structurally altered gas molecule is a combination of two parts hydrogen and one part oxygen. The structurally altered gas molecule has a hydrogen-oxygen-hydrogen bond angle between 94 degrees and 104 degrees and hydrogen-oxygen bond length between 0.95 Angstrom and 1.3 Angstrom.

In block 1304, the method 1300 proceeds with infusing the structurally altered gas molecules into a living organism. Upon being infused, the structurally altered gas molecules cause an increase of production of the ATP in the living organism.

In an example embodiment, upon being infused in water containing mitochondria, the structurally altered gas molecules cause an increase in maximum rates of phosphorylating respiration of the mitochondria by 13%. In some example embodiments, upon being infused in water supplied to horses, the structurally altered gas molecules cause an increase in runtime of the horses by 2 minutes on average.

In an example embodiment, upon being infused in water supplied to horses, the structurally altered gas molecules cause an increase in a maximum rate of oxygen consumption of the horses by 5% during running. In some example embodiments, upon being infused in water supplied to seeds of tomatoes, the structurally altered gas molecules cause a decrease in a time of formation of fruits of the tomatoes by 22%.

In an example embodiment, upon being infused in water supplied to seeds of tomatoes, the structurally altered gas molecules cause an increase of complete germination of the seeds by 22%. In some example embodiments, upon being infused in water supplied to seeds of tomatoes, the structurally altered gas molecules cause an increase of production of fruits of the tomatoes by 125% in volume of the fruits. In an example embodiment, upon being infused in the water, the structurally altered gas molecules cause a shift in redox potential of the water from 0 millivolts −200 millivolts.

Thus, systems and methods for enhancing production of ATP in living organisms have been described. Although embodiments have been described with reference to specific example embodiments, it will be evident that various modifications and changes can be made to these example embodiments without departing from the broader spirit and scope of the present application. Accordingly, the specification and drawings are to be regarded in an illustrative rather than a restrictive sense.

What is claimed is:

1. A method for improving the general cellular function in living organisms, the method comprising:

generating structurally altered gaseous water molecules from water, wherein the structurally altered gaseous water molecules have a higher probability of attraction of electrons into areas adjunct to the structurally altered gaseous water molecules than molecules of the water; and infusing the structurally altered gaseous water molecules into a liquid and supplying the liquid to a living organism, wherein, upon being infused and supplied, the structurally altered gaseous water molecules cause an improvement in the general cellular function in the living organism, wherein the generation of structurally altered gaseous water molecules includes:

placing an electrolyte solution in a chemical reaction chamber;

adding purified water to the chemical reaction chamber; and applying a focused magnetic field and an electric field to a mixture of the purified water and the electrolyte solution to cause generation of the structurally altered gaseous water molecules from the purified water, wherein:

a structurally altered gaseous water molecule of the structurally altered gaseous water molecules is a combination of two parts hydrogen and one part oxygen; and the structurally altered gaseous water molecule has a hydrogen-oxygen-hydrogen bond angle between 94 degrees and 104 degrees and hydrogen-oxygen bond length between 0.95 Angstrom and 1.3 Angstrom.

2. The method of claim 1, wherein the liquid is water and, upon infusing the structurally altered gaseous water molecules in the water, the water has a shift in redox potential from 0 millivolts to −200 millivolts.

* * * * *